United States Patent [19]

Sanchez

[11] 4,043,940

[45] Aug. 23, 1977

[54] LIQUID ACYL SULFONYL PEROXIDE FORMULATIONS DERIVED FROM SOLID ACYL ALKYLSULFONYL PEROXIDES

[75] Inventor: Jose Sanchez, Grand Island, N.Y.

[73] Assignee: Pennwalt Corporation, Philadelphia, Pa.

[21] Appl. No.: 596,115

[22] Filed: July 15, 1975

[51] Int. Cl.$^2$ .................... C08F 4/34; C07C 179/06
[52] U.S. Cl. .................................... 252/426; 252/186; 260/610 R; 526/213; 526/223; 526/330; 526/345
[58] Field of Search .......... 260/610 A, 610 R, 610 D, 260/610 SC, 87.5 C, 607; 252/186, 426

[56] References Cited

U.S. PATENT DOCUMENTS

| | | | |
|---|---|---|---|
| 3,466,255 | 9/1969 | Faerber et al. | 260/610 R |
| 3,541,026 | 11/1970 | Shaaf et al. | 252/426 |
| 3,586,722 | 6/1971 | Sanchez | 260/80 C |
| 3,650,972 | 3/1972 | Sanchez | 252/186 |

*Primary Examiner*—James O. Thomas, Jr.
*Assistant Examiner*—W. B. Lone

[57] ABSTRACT

Storage stable liquid compositions are prepared from solid acyl alkylsulfonyl peroxides and polar or polarizable solvents or solvent mixtures. The compositions are liquid at 0° to −40° C and are useful as free-radical initiators for polymerizaton of vinyl monomers.

18 Claims, No Drawings

LIQUID ACYL SULFONYL PEROXIDE FORMULATIONS DERIVED FROM SOLID ACYL ALKYLSULFONYL PEROXIDES

BACKGROUND OF THE INVENTION

1. Field of the Invention

This invention relates to compositions prepared from solid acyl alkysulfonyl peroxides and polar or polarizable solvents or solvent mixtures. These novel compositions are used as free-radical initiators for vinyl monomer polymerization processes.

2. Description of Prior Art

Acyl sulfonyl peroxides such as acetyl cyclohexylsulfonyl peroxide (ACSP) have found increasing use in polymerization and copolymerization of vinyl monomers such as vinyl chloride and vinyl acetate. These initiators are especially useful for increasing the output of polyvinylchloride (PVC) reactors when used in combination with dialkyl peroxydicarbonates. Normally, a vinyl chloride polymerization which employs only a dialkyl peroxydicarbonate suffers through an initial induction period in which little PVC is produced. By using acyl sulfonyl peroxides such as ACSP in combination with dialkyl peroxydicarbonates a rapid polymerization occurs initially which then continues throughout the polymerization. This results in a shorter polymerization cycle, an increased rate of production of PVC and greater production of PVC from PVC reactors.

Although acyl sulfonyl peroxides are quite useful in vinyl chloride polymerizations, they are shock sensitive in the pure form. Hence, they have to be diluted in some manner for safe handling. Acetyl cyclohexylsulfonyl peroxide (ACSP) is currently the only acyl sulfonyl peroxide on the market that is available in commercial quantities. Since ACSP in pure form is a shock sensitive solid (melting point, 33°-35° C), three dilutions of ACSP are commercially available, they are: (a) a 28-30% solution of ACSP in dimethyl phthalate (DMP), (b) a 20% solution in toluene, and (c) a 65% wetted solid. All three formulations have one or more detrimental properties.

The 29% solution of ACSP in DMP has a very narrow recommended storage temperature range of −5° to −9° C. The upper temperature limit was set by thermal stability restrictions whereas the lower temperature limit was set by phase stability restrictions, that is, solids formed at temperatures at or below −9° C. Therefore, the producer as well as the users of this formulation are forced to maintain expensive storage facilities that maintain the temperature between −5° and −9° C. Now recognized is a possible hazard associated with this formulation when stored below −9° C. Unexpected decompositions are possibile if this formulation is stored at −15° to −30° C. Apparently, DMP (m.p., 2° C) can crystallize thus increasing the concentration of ACSP in the supernatant liquid at −15° to −30° C. ACSP could then massively and rapidly crystallize from the supernatant liquid thus increasing the temperature of the system to the melting point of ACSP (33° - 35° C) which is above the decomposition temperature of ACSP (18° C). A rapid decomposition is then possible.

The 20% solution of ACSP in toluene contains 80% toluene. This high level of toluene would discourage use of this formulation for producing polyvinyl chloride (PVC) which would be used in food applications. In addition, spillage of this formulation could be hazardous because of the evaporation of low boiling toluene (b.P., 108°-110° C), thus leaving a shock sensitive solid residue. Furthermore, this formulation is significantly less stable than the 28-30% ACSP in DMP and readily develops color during storage.

The 65% wetted solid is not homogenous and is an extremely difficult formulation to handle. Because of the low thermal stability of ACSP, the 65% wetted solid must be stored below 0° C resulting in a solid block because of the water freezing. In this form it must be thawed or hazardously broken-up prior to use. Unlike the liquid formulations the 65% wetted solid cannot be pumped into polymerization reactors.

In order to overcome the detrimental properties of the various ACSP formulations two liquid acyl alkylsulfonyl peroxides, acetyl secheptylsulfonyl peroxide and acetyl 1-methylcyclohexysulfonyl peroxide, were offered for use. However, these peroxides are shock sensitive liquids and have only been offered as safe 50% liquid formulations in solvents such as DMP and isobutyl isobutyrate. These formulations have not been found by the PVC industry as acceptable replacements for the ACSP formulations with their faults.

U.S. Pat. Nos. 3,650,972, 3,466,255 and 3,340,243 disclose prior art acyl sulfonyl peroxide formulations.

SUMMARY OF THE INVENTION

This invention concerns:

A. A liquid solution composition which is a safe storable stable liquid at 0° to −40° C consisting essentially of:

a. 10 to 70% by weight of a solid acyl alkylsulfonyl peroxide with a melting point of −10° to about 70° C having the formula

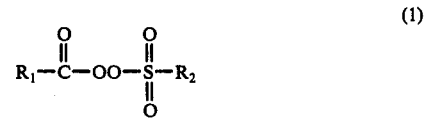

(1)

where
1. $R_1$ is an alkyl of 1 to 4 carbons and
2. $R_2$ is selected from the group consisting of an alkyl or monochloroalkyl radical of 3 to 18 carbons and a cycloalkyl or cyclomonochloroalkyl radical of 4 to 12 carbons; and b. 90 to 30% of a polar or polarizable solvent or solvent system having a complete solidification temperature below about −10° C and a miscibility number greater than 8 and less than 21. This solvent or solvent system has at least about 20% by weight based on the solid acyl sulfonyl peroxide of a solvent which has a boiling point of at least 165° C at 760 torr. (Note that 1 torr is equal to 1 mm of mercury of pressure.)

The term "complete solidification temperatures" is defined as the temperatures below which a liquid phase is absent and above which a liquid phase is present. It corresponds to the melting point when a pure solvent is employed. A polar solvent is defined as a solvent which has at least one polar bond in its structure, that is, a bond created between two atoms with different electronegativities, bonds such as C—O, C—N, C—Cl, O—H, N—O, etc. Carbon tetrachloride can be considered as a polar solvent under this definition even though it does not possess a dipole moment. A polarizable solvent is one which has pi ($\pi$) electrons which can be distorted (polarized) by a polar solute such as a solid acyl alkylsulfonyl peroxide. Hence, an attractive interaction occurs between the polarizable solvent and the polar solute which then leads to dissolution of the solute. It is this interaction which allows benzene to solvate polar compounds. Certain solvents can be both polar and polarizable solvents.

B. Processes using the novel improved liquid acyl alkylsulfonyl peroxide formulations described above as initiators for polymerizing ethylenically unsaturated monomers, such as, vinyl chloride, vinyl acetate and methyl methacrylate, which monomers are responsive at suitable temperatures to initiating amounts of these liquid formulations.

DETAILED DESCRIPTION OF THE INVENTION

It has now been surprisingly found that improved liquid ACSP formulations with wider storage temperature ranges and, optionally, higher ACSP levels can be obtained when certain polar or polarizable solvents or polar or polarizable solvent mixtures are employed in these formulations.

| Examples: Formulation | ACSP, % | Solvent, % | (Cosolvent) Second Solvent, % |
|---|---|---|---|
| I | 30 | DMP, 55 | DEP[1], 15 |
| II | 35 | DMP, 51 | DEP, 14 |
| III | 40 | DMP, 47 | DEP, 13 |
| IV | 30 | DMP, 55 | 4-Butyrolactone, 15 |
| V | 30 | $CH_2Cl_2$, 56 | DMP, 14 |
| VI | 30 | $CH_2Cl_2$, 56 | 4-Butyrolactone, 14 |
| VII | 30 | DMP, 35 | Ethyl acetate, 35 |
| VIII | 30 | 4-Butyrolactone, 70 | None |

[1]DEP is diethyl phthalate.

These compositions are shock stable, are thermally stable at 0° to −10° C and remain homogeneous liquids at 0° to −40° C whereas the prior art compositions of 30% ACSP in DMP (similar to the commercial 28–30% ACSP formulation) and 30% ACSP in DEP solidify significantly above −40° C. The improved liquid ACSP formulations have also been found to be as efficient in vinyl chloride (VCl) suspension polymerizations as the commercial ACSP formulations and, because of their widened storage and handling temperature range, they have been found to be more easily handled during the initial stages of the VCl polymerization processes than the commercial ACSP formulations. In addition, most of the improved 30% or higher ACSP liquid formulations of this invention were found to have lower viscosities than the commercial 28–30% ACSP/DMP liquid formulation. Lower viscosity is an important initiator property since pumping of the initiator is, therefore, easier and initiator containers are more quickly and more completely emptied.

It should be emphasized that the acyl sulfonyl peroxides (1) utilized in the compositions of this invention are solids (m.p., above −10° C). Illustrative solid acyl alkylsulfonyl peroxides (1) which come under the definition of (1) are: acetyl t-amylsulfonyl peroxide (m.p., about 5° C), acetyl t-butylsulfonyl peroxide (m.p., 35°-37° C), acetyl 3-chloro-1-methylpropylsulfonyl peroxide (m.p., 32°-33° C) and ACSP (m.p., 33°-35° C).

The compositions of this invention include, in addition to the solid acyl alkylsulfonyl peroxide (1), a polar or polarizable liquid solvent or a polar or polarizable solvent mixture. The solvent or solvent mixture must have sufficient attraction for the solid acyl alkylsulfonyl peroxide such that the compositions of this invention will exhibit no solid formation or phase separation at temperatures of about 0° C to −40° C, which includes the ordinary storage temperature used in industry for storage of acyl alkylsulfonyl peroxides. A measure of the attraction of solid acyl alkylsulfonyl peroxide and solvent or solvent mixture for each other was described in the June 1972 edition of Chemical Technology (pages 359-363) by N. B. Godfrey. Godfrey introduced the concept of solvent selection by miscibility number (M) and listed the M numbers for approximately 400 organic liquids. The higher the M number the higher the lipophilic (affinity for oil-like substances) character of the organic liquid. Normally, two liquids which have M numbers which differ by less than 15 units are miscible in all proportions at 25° C. Occasionally this relationship broke down, i.e., the M number range was less than 31. Therefore, Godfrey gave these solvents dual M numbers. The lower M number was used for predicting miscibility of the selected solvent with more lipophilic solvents whereas the higher M number was used for predicting miscibility of the selected solvent with less lipophilic solvents. For instance, adiponitrile has the dual M numbers 8 and 19. At 25° C adiponitrile will be completely miscible with solvents having M numbers between 23 (i.e., 8+15) and 4 (i.e., 19−15).

Based on the M numbers listed by Godfrey for sulfonyl compounds acyl alkylsulfonyl peroxides have been assigned the dual M numbers 12 and 17. At 25° C normally liquid acyl alkylsulfonyl peroxides will be completely miscible with high lipophilic solvents with M numbers up to 27 (i.e., 12+15) and with low lipophilic solvents having M numbers down to about 2 (17−15). However, because of strong hydrogen-bonding interactions of the lower glycols, the liquid acyl alkylsulfonyl peroxides display anomalous miscibility behavior with the lower glycols (M numbers of 2−4) and are not miscible in all proportions at 25° C.

The compositions of this invention, however, deal with improved liquid acyl alkylsulfonyl peroxide formulations which are derived from solid (m.p., between −10° C and 70° C) rather than liquid acyl alkylsulfonyl peroxides. In addition, this invention deals with the miscibility of solvent or solvent systems and solid acyl alkylsulfonyl peroxides at 0° C or lower rather than at 25° C. In general it has been found that solvents or solvent mixtures which have M numbers differing by less than 9 units from those of the acyl alkylsulfonyl peroxides (12, 17) will produce stable liquid acyl alkylsulfonyl peroxide solutions which contain 10 to 70%, preferably 25 to 60%, of solid acyl alkylsulfonyl peroxide at 0° to −40° C. Therefore, solvents or solvent mixtures which are in the M number range of greater than 8 and less than 21 will generally exhibit sufficient solvation power to produce liquid acyl alkylsulfonyl peroxide compositions at 0° C to −40° C which contain 10 to 70%, preferably 25 to 60%, of solid (m.p., between −10° and 70° C) acyl alkylsulfonyl peroxide.

Solvents having M numbers outside the range of greater than 8 and less than 21 have been found to be poor solvents for solid acyl alkylsulfonyl peroxides at 0° to −40° C because of the low solubility of solid acyl alkylsulfonyl peroxides in these solvents. For instance, dioctyl phthalate (M number = 24), cyclohexane (M number = 28), isobutyl isobutyrate (M number = 23) and ethylene glycol (M number = 2) were poor solvents for ACSP.

In addition to the M number requirement, the useful solvent or solvent system should have a complete solidification temperature below about −10° C. The complete solidification temperature of a pure solvent corresponds to the melting point of that solvent whereas the complete solidification temperature of a solvent mixture corresponds to the temperature below which a liquid phase is absent and above which a liquid phase is present in the solvent mixture. The complete solidification temperature of a solvent system will generally correspond to a temperature lower than the melting point of the pure solvent components. If the complete solidification temperature of the solvent or solvent system is above −10° C, the liquid acyl alkylsulfonyl peroxide formulation which is made from a solid acyl alkylsulfonyl peroxide and the solvent system will separate into phases (solid and liquid) or will solidify when the composition is stored below about −20° C. For instance, it has been found that the commercial liquid ACSP formulation (28-30% ACSP/70-72% DMP) started to solidify after 2 weeks at −23° C even though DMP had M numbers of 12 and 19. The liquid above the solid actually increased in ACSP concentration (supersaturated at −23° C); hence, the solvent DMP (m.p.,2° C) came out of solution first. The same phenomenon occurred with a 30% ACSP/70% DEP formulation. Furthermore, when a 62/8 mixture of DMP/DEP, which had a complete solidification temperature of about −7° C, was used to produce a 30%ACSP/62% DMP/8% DEP formulation, the formulation solidified at −45° C. A 55/15 mixture of DMP/DEP, which had a complete solidification temperature below −28° C, produced a 30% ACSP/55% DMP/b 15% DEP formulation in which no solid formation or phase separation occurred after 20 weeks at −45° C.

In addition to the M number and the complete solidification temperature requirements for the solvents or solvent systems employed, sufficient solvent with a boiling point above about 165° C at 760 torr should be present in order to suppress residue impact shock sensitivity. For instance, it has been found that 30% ACSP/70% CH$_2$Cl$_2$ is phase stable (no solidification) after 17 weeks at −50° C. Since CH$_2$Cl$_2$ has an M number of 20 and a melting point of −97° C, it should be and is a good solvent for ACSP. However, its boiling point is only 40° C, thus, if the 30% ACSP/70% CH$_2$Cl$_2$ formulation is spilled CH$_2$Cl$_2$ rapidly evaporates leaving behind a nearly pure, shock sensitive ACSP residue. It has been found that this shock hazard is suppressed by incorporating in the formulation about 20% by weight, based on solid acyl alkylsulfonyl peroxide, of a solvent which boils above about 165° C at 760 torr.

In restating the above-mentioned requirement of the invention, the invention is directed to improved liquid acyl alkylsulfonyl peroxide compositions which are storable liquids at 0° C to −40° C. These compositions should contain 10 to 70% (preferably 25 to 60%) of a solid acyl alkylsulfonyl peroxide having the formula

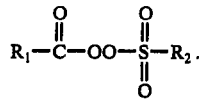

This peroxide should have a melting point in the range of between −10° C and 70° C. $R_1$ is an alkyl of 1 to 4 carbons such as methyl, ethyl or butyl. $R_2$ is an alkyl or chloroalkyl radical having 3 to 18 carbons, normally 3 to 8 carbons with the most preferred range being 3 to 6 carbons, or a cycloalkyl or cyclochloroalkyl radical of 4 to 12 carbons. The chlorosubstituted alkyl and cycloalkyl groups are normally mono-substituted groups.

The compositions include 90 to 30% (preferably 75 to 40%) by weight of a polar or polarizable solvent or solvent system having a complete solidification temperature below −10° C and an M number of greater than 8 and less than 21. The solvent or solvent system should possess at least about 20% by weight based on solid acyl alkylsulfonyl peroxide of a solvent or solvent system which boils above 165° C at 760 torr.

More than two polar or polarizable solvent can be used to produce the improved liquid acyl alkylsulfonyl peroxide formulations of this invention as long as the criteria for boiling point, complete solidification temperature and M number are essentially met. Similar formulations using liquid acyl alkylsulfonyl peroxides can also be made employing similar solvents or solvent systems.

A list of polar or polarizable solvents according to class of compound and coming within the broad scope is given hereinafter for purpose of illustration and not as any limitation on the scope of the invention.

POLAR SOLVENTS a. Haloaromatic hydrocarbons and nitroaromatic hydrocarbons, such as, monochlorobenzene, dichlorobenzene, nitrobenzene and chlorotoluene.

b. Polyhaloalkanes and polyhaloalkenes, such as, carbon tetrachloride, trichloroethane, methylene chloride, ethylene dichloride, trichloroethylene, perchloroethylene and propylene dichloride.

c. Alkyl cyanides having 2–4 carbon atoms, such as, acetonitrile, propionitrile and butyronitrile. Aryl nitriles such as benzonitrile.

d. Dialkyl ethers and heterocyclic ethers having only carbon and oxygen in the ring, such as, diethyl ether, ethyl isopropyl ether, dibutyl ether, furan, tetrahydrofuran and dioxane.

e. Lower alkanols and lower alkoxyalkanols (ether alcohols), such as, methanol, ethanol, isopropanol, sec-butanol, methoxybutyl alcohol and tetrahydrofurfuryl alcohol.

f. Lower alkanones and cycloalkanones, such as, acetone, methyl ethyl ketone, dibutyl ketone, pentanone, cyclohexanone, trimethyldihydroisophorone, and diacetone alcohol.

g. Alkyl esters of alkanoic acids, alkanedioic acids, alkanetrioic acids, alkenoic acids, ketoacids, alkenedioic acids, cycloalkanoic acids, aryl carboxylic acids and aryl dicarboxylic acids, such as, methyl acetate, ethyl acetate, butyl acetate, amyl acetate, octyl acetate, isobutyl isobutyrate, butyl propionate, ethyl acetoacetate, dioctyl adipate, didecyl adipate, diethyl carbonate, diethyl maleate, dibutyl maleate, dibutyl sebacate, diisobutyl adipate, dioctyl azelate, ethyl lactate, butyl lactate, triethyl citrate, tributyl citrate, dimethyl phthalate, diethyl phthalate, dibutyl phthalate, di(methoxyethyl) phthalate, ethyl methyl phthalate, isopropyl methyl phthalate and mixed alkyl phthalate esters made from mixtures of alcohols having 7, 9 and 11 carbons or from mixtures of alcohols having 6, 8, and 10 carbons.

h. Cyclic esters such as 3-butyrolactone, 4-butyrolactone and propylene carbonate.

i. Carboxylate esters of alkanediols such as the mono- and diisobutyrate esters of 2,2,4-trimethyl-1,3-pentanediol, ethylene glycol diacetate, ethylene glycol mono butyl ether acetate, diethylene glycol mono butyl ether acetate, diethylene glycol mono ethyl ether acetate and ethylene glycol mono ethyl ether acetate.

j. Trialkyl phosphates, tri(alkoxyalkyl) phosphates, triaryl phosphates, triaralkyl phosphates and halogenated trialkyl and triaralkyl phosphates such as trimethyl phosphate, triethyl phosphate, tributyl phosphate, tri(butoxyethyl) phosphate, tricresyl phosphate, tri-(2-chloroethyl) phosphate and tri-(2,3-dibromopropyl) phosphate.

k. Amides derived from carboxylic acids or phosphoric acids such as N,-N-dimethylformamide, N,N-dimethylacetamide, N-methyl-2-pyrrolidone and hexamethylphosphoramide.

POLARIZABLE SOLVENTS

Aromatic hydrocarbons, haloaromatic hydrocarbons and nitroaromatic hydrocarbons, such as:

benzene
toluene
ethylbenzene
cumene
xylene
α-methylstyrene
monochlorobenzene
chlorotoluene
dichlorobenzene
nitrobenzene
methylnaphthalenes Several of the above are also polar solvents.

Table I summarizes M numbers, boiling points, melting points and water solubilities of various polar or polarizable solvents which were employed in the practice of this invention.

Table I
M Numbers, Boiling Points, Melting Points and Water Solubilities of Various Polar and Polarizable Solvents

| Solvent | Godfrey[1] M Number | Boiling Point[2] (B.P.), °C | Melting Point (M.P.), °C | Solvent Water solubility[3] |
|---|---|---|---|---|
| Dimethyl phthalate (DMP) | 12, 19 | 283 | 2 | Insol. |
| Diethyl phthalate (DEP) | 13, 20 | 295 | −0.3 | Insol. |
| Ethyl methyl phthalate | (est.) 12, 20 | >283 | — | Insol. |
| Dibutyl phthalate (DBP) | 22 | 325 | −35 | Insol. |
| Triethyl citrate | (est.) 16 | 294 | — | Insol. |
| Butyl lactate | (est.) 15 | 188 | −43 | Insol. |
| Ethyl lactate | 14 | 154 | −25 | Soluble |
| Dioctyl adipate | (est.) 21 | 224(10) | <−70 | Insol. |
| Dibutyl maleate | 22 | 225 | — | Insol. |
| Isobutyl isobutyrate | 23 | 149 | −81 | Insol. |
| Texanol[4] | (est.) 17 | 180(125) | −50 | Insol. |
| 2-Ethylhexyl acetate | (est.) 22 | 198.5 | −93 | Insol. |
| n-Butyl acetate | 22 | 125 | −78 | Insol. |
| 4-Butyrolactone | 10 | 204 | −45 | Soluble |
| Ethyl acetoacetate | 13, 19 | 181 | −43 | Soluble |
| Diacetone alcohol | 14 | 169 | −43 | Soluble |
| Diisobutyl ketone | 23 | 163–173 | −46 | Insol. |
| Tetrahydrofurfuryl alcohol | 13 | 178 | −80 | Soluble |
| N,N-Dimethylacetamide | 13 | 164–166 | −20 | Soluble |
| N-Methyl-2-pyrrolidone | 13 | 202 | −24.4 | Soluble |
| Tetramethylurea | 15 | 177 | −1 | Soluble |
| Hexamethylphosphoramide | 15 | 230–232(740) | 6–8 | Soluble |
| Phosflex 500[5] | (est.) 22 | >200 | <−78 | Insol. |
| Tricresyl phosphate (TCP) | 21 | 260–275(10) | <−35 | Insol. |
| $CH_2Cl_2$ | 20 | 40 | −97 | Insol. |
| Acetone | 15, 17 | 56.5 | −95 | Soluble |
| Ethyl acetate | 19 | 77 | −84 | Insol. |
| Acetonitrile | 11, 17 | 80 | −45 | Soluble |
| Toluene | 23 | 111 | −95 | Insol. |
| Propylene carbonate | 9, 17 | 242.1 | −73.1 | Soluble |

Footnotes:
[1] N.B. Godfrey, Chemical Technology, June 1972, 359–363. Est. values are estimated from values listed for similar compounds.
[2] Numbers in parentheses are pressure values in units of torr.
[3] Soluble if greater than 10%, Insol. if less than 10%.
[4] Texanol - The monoisobutyrate of 2,4,4-trimethyl-1,3-pentanediol, manufactured by Eastman Kodak Company.
[5] Phosflex 500 - A chlorinated triaralkyl phosphate manufactured by the Stauffer Chemical Company.

Typical improved liquid acyl sulfonyl formulations which are derived from solid-acyl alkylsulfonyl peroxides and various polar or polarizable solvents or solvent systems having M numbers in the range of greater than 8 and less than 21 are summarized in Table II. It should be emphasized that Table II does not exhaustively list all of the possible attractive liquid acyl alkylsulfonyl peroxide formulations of this invention. Other liquid acyl alkylsulfonyl peroxide formulations which are derived from solid acyl alkylsulfonyl peroxides and polar or polarizable solvents or solvent mixtures are possible which similarly have improved storage temperature ranges, safety and handling characteristics when compared to the commercial liquid ACSP formulations. It should also be noted that several of the compositions of this invention (TABLE II) employ more than two solvents.

The M numbers listed in Table II for single solvents were taken from or were estimated from the data in the Godfrey reference mentioned above. A weighted average of M numbers was employed when two or more solvents were employed. If a solvent pair both had dual M numbers weighted averages of the higher numbers and of the lower numbers were calculated to give dual M numbers for the solvent mixture. If a solvent pair consisted of a solvent with a single M number and a solvent with dual M numbers, dual M numbers for the solvent mixture were calculated using weighted averages of the single M number of one solvent with the upper and lower M numbers of the other solvent.

Table II

Improved Liquid Acyl Alkylsulfonyl Peroxide Formulations Derived from Solid Acyl Alkylsulfonyl Peroxides

| Composition | Peroxide, % | Solvent, % | Second Solvent, % | M Number |
|---|---|---|---|---|
| A | ACSP, 30 | DMP, 60 | DEP, 10 | 12.1,19.1 |
| B | ACSP, 30 | DMP, 55 | DEP, 15 | 12.2,19.2 |
| C | ACSP, 30 | DMP, 45 | DEP, 25 | 12.4,19.4 |
| D | ACSP, 30 | DMP, 35 | DEP, 35 | 12.5,19.5 |
| E | ACSP, 30 | DMP, 25 | DEP, 45 | 12.6,19.6 |
| F | ACSP, 35 | DMP, 51 | DEP, 14 | 12.2,19.2 |
| G | ACSP, 40 | DMP, 47 | DEP, 13 | 12.2,19.2 |
| H | ACSP, 45 | DMP, 43 | DEP, 12 | 12.2,19.2 |
| I | ACSP, 40 | DMP, 30 | DEP, 30 | 12.5,19.5 |
| J | ACSP, 30 | DMP, 55 | Diacetone alcohol, 15 | 12.4,17.9 |
| K | ACSP, 30 | DMP, 55 | Tetrahydrofurfuryl alcohol, 15 | 12.2,17.7 |
| L | ACSP, 30 | DMP, 55 | Ethyl acetoacetate, 15 | 12.2,19.0 |
| M | ACSP, 30 | DMP, 55 | Tetramethylurea, 15 | 12.6,18.1 |
| N | ACSP, 30 | DMP, 55 | Hexamethylphosphoramide, 15 | 12.6,18.1 |
| O | ACSP, 30 | DMP, 55 | Dimethylacetamide, 15 | 12.2,17.7 |
| P | ACSP, 30 | DMP, 55 | N-Methyl-2-pyrrolidone, 15 | 12.2,17.7 |
| Q | ACSP, 30 | DMP, 55 | Triethyl citrate, 15 | 12.9,18.4 |
| R | ACSP, 30 | DMP, 55 | Butyl lactate, 15 | 12.6,18.1 |
| S | ACSP, 30 | DMP, 55 | Dioctyl adipate, 15 | 13.9,19.4 |
| T | ACSP, 30 | DMP, 65 | 4-Butyrolactone, 5 | 11.9,18.4 |
| U | ACSP, 30 | DMP, 60 | 4-Butyrolactone, 10 | 11.7,17.7 |
| V | ACSP, 30 | DMP, 55 | 4-Butyrolactone, 15 | 11.6,17.1 |
| W | ACSP, 30 | DMP, 35 | 4-Butyrolactone, 35 | 11.0,14.5 |
| X | ACSP, 30 | DMP, 25 | 4-Butyrolactone, 45 | 10.7,13.2 |
| Y | ACSP, 35 | DMP, 55 | 4-Butyrolactone, 10 | 11.7,17.6 |
| Z | ACSP, 35 | DMP, 50 | 4-Butyrolactone, 15 | 11.5,16.9 |
| AA | ACSP, 40 | DMP, 40 | 4-Butyrolactone, 20 | 11.3,16.0 |
| AB | ACSP, 30 | 4-Butyrolactone, 70 | — | 10 |
| AC | ACSP, 40 | 4-Butyrolactone, 60 | — | 10 |
| AD | ACSP, 50 | 4-Butyrolactone, 50 | — | 10 |
| AE | ACSP, 70 | 4-Butyrolactone, 30 | — | 10 |
| AF | ACSP, 30 | DEP, 55 | 4-Butyrolactone, 15 | 12.4,17.9 |
| AG | ACSP, 30 | DEP, 35 | 4-Butyrolactone, 35 | 11.5,15.0 |
| AH | ACSP, 40 | DEP, 40 | 4-Butyrolactone, 20 | 12.0,16.7 |
| AI | ACSP, 30 | $CH_2Cl_2$, 56 | Butyl lactate, 14 | 19.0 |
| AJ | ACSP, 30 | $CH_2Cl_2$, 56 | Triethyl citrate, 14 | 19.2 |
| AK | ACSP, 30 | $CH_2Cl_2$, 56 | DMP, 14 | 18.4,19.8 |
| AL | ACSP, 30 | $CH_2Cl_2$, 56 | Dibutyl phthalate, 14 | 20.4 |
| AM | ACSP, 30 | $CH_2Cl_2$, 56 | DEP, 14 | 18.6,20.0 |
| AN | ACSP, 30 | $CH_2Cl_2$, 56 | Phosflux 500[1], 14 | 20.4 |
| AO | ACSP, 30 | $CH_2Cl_2$, 56 | Tricresyl phosphate, 14 | 20.2 |
| AP | ACSP, 30 | $CH_2Cl_2$, 56 | Texanol[2], 14 | 19.4 |
| AQ | ACSP, 30 | $CH_2Cl_2$, 63 | 4-Butyrolactone, 7 | 19.0 |
| AR | ACSP, 30 | $CH_2Cl_2$, 56 | 4-Butryolactone, 14 | 18.0 |
| AS | ACSP, 30 | $CH_2Cl_2$, 40 | 4-Butyrolactone, 30 | 15.7 |
| AT | ACSP, 40 | $CH_2Cl_2$, 30 | 4-Butyrolactone, 30 | 15.0 |
| AU | ACSP, 35 | $CH_2Cl_2$, 51 | 4-Butyrolactone, 14 | 17.8 |
| AV | ACSP, 40 | $CH_2Cl_2$, 46 | 4-Butyrolactone, 14 | 17.7 |
| AW | ACSP, 35 | $CH_2Cl_2$, 51 | DMP, 14 | 18.3,19.8 |
| AX | ACSP, 40 | $CH_2Cl_2$, 46 | DMP, 14 | 18.1,19.8 |
| AY | ACSP, 35 | $CH_2Cl_2$, 51 | DEP, 14 | 18.5,20.0 |
| AZ | ACSP, 40 | $CH_2Cl_2$, 46 | DEP, 14 | 18.4,20.0 |
| BA | ACSP, 35 | $CH_2Cl_2$, 51 | Dibutyl phthalate, 14 | 20.4 |
| BB | ACSP, 40 | $CH_2Cl_2$, 46 | Dibutyl phthalate, 14 | 20.5 |
| BC | ACSP, 35 | $CH_2Cl_2$, 51 | Triethyl citrate, 14 | 19.1 |
| BD | ACSP, 40 | $CH_2Cl_2$, 46 | Triethyl citrate, 14 | 19.1 |
| BE | ACSP, 35 | $CH_2Cl_2$, 51 | Butyl lactate, 14 | 18.9 |
| BF | ACSP, 40 | $CH_2Cl_2$, 46 | Butyl lactate, 14 | 18.8 |
| BG | ACSP, 15 | $CH_2Cl_2$, 60 | 4-Butyrolactone, 25 | 17.1 |
| BH | ACSP, 15 | $CH_2Cl_2$, 80 | DMP, 5 | 19.5,19.9 |
| BI | ACSP, 10 | $CH_2Cl_2$, 85 | DMP, 5 | 19.6,19.9 |
| BJ | ACSP, 10 | $CH_2Cl_2$, 80 | 4-Butyrolactone, 10 | 18.9 |
| BK | ACSP, 35 | $CH_2Cl_2$, 51 | Phosflex 500[1], 14 | 20.4 |
| BL | ACSP, 40 | $CH_2Cl_2$, 46 | Phosflex 500[1], 14 | 20.5 |
| BM | ACSP, 30 | $CH_2Cl_2$, 35 | DMP, 35 | 16.0,19.5 |
| BN | ACSP, 30 | DMP, 35 | Acetone, 35 | 13.5,18.0 |
| BO | ACSP, 30 | DMP, 35 | Ethyl acetate, 35 | 15.5,19.0 |
| BP | ATASP[3], 30 | DMP, 55 | DEP, 15 | 12.2,19.2 |
| BQ | ATASP[3], 30 | DMP, 55 | 4-Butyrolactone, 15 | 11.6,17.1 |
| BR | ATBSP[4], 30 | DMP, 55 | DEP, 15 | 12.2,19.2 |
| BS | ATBSP[4], 30 | DMP, 55 | 4-Butyrolactone, 15 | 11.6,17.1 |
| BT | ACMPSP[5], 30 | DMP, 55 | DEP, 15 | 12.2,19.2 |
| BU | ACMPSP[5], 30 | DMP, 55 | 4-Butyrolactone, 15 | 11.6,17.1 |
| BV | ATASP[3], 30 | 4-Butyrolactone, 70 | — | 10 |
| BW | ATBSP[4], 30 | 4-Butyrolactone, 70 | — | 10 |
| BX | ACMPSP[5], 30 | 4-Butyrolactone, 70 | — | 10 |
| BY | ATASP[3], 30 | DMP, 35 | DEP, 35 | 12.5,19.5 |
| BZ | ATASP[3], 30 | DMP, 52.5 | 4-Butyrolactone, 17.5 | 11.5,16.8 |
| CA | ATASP[3], 40 | DMP, 30 | 4-Butyrolactone, 30 | 11.0,14.5 |
| CB | ATASP[3], 40 | DMP, 30 | DEP, 30 | 12.5,19.5 |
| CC | ATBSP[4], 40 | DMP, 30 | 4-Butyrolactone, 30 | 11.0,14.5 |
| CD | ATBSP[4], 40 | DMP, 30 | DEP, 30 | 12.5,19.5 |
| CE | ACSP, 30 | Ethyl methyl phthalate, 70 | — | 12,20 |
| CF | ACSP, 40 | Ethyl methyl phthalate, 60 | — | 12,20 |
| CG | ATASP[3], 30 | Ethyl methyl phthalate, 70 | — | 12,20 |
| CH | ATASP[3], 40 | Ethyl methyl phthalate, 60 | — | 12,20 |
| CI | ATBSP[4], 30 | Ethyl methyl phthalate, 70 | — | 12,20 |
| CJ | ATBSP[4], 40 | Ethyl methyl phthalate, 60 | — | 12,20 |
| CK | ACSP, 32 | Ethyl methyl phthalate, 34 | DEP, 17 plus DMP, 17 | 12.3,19.8 |
| CL | ACSP, 30 | 4-Butyrolactone, 10 | DEP, 30 plus DMP, 30 | 12.1,18.1 |

Table II-continued
Improved Liquid Acyl Alkylsulfonyl Peroxide Formulations Derived from Solid Acyl Alkylsulfonyl Peroxides

| Composition | Peroxide, % | Solvent, % | Second Solvent, % | M Number |
|---|---|---|---|---|
| CM | ACSP, 30 | 4-Butyrolactone, 20 | DEP, 25 plus DMP, 25 | 11.8,16.8 |
| CN | ACSP, 40 | 4-Butyrolactone, 10 | DEP, 25 plus DMP, 25 | 12.1,17.9 |
| CO | ACSP, 40 | 4-Butyrolactone, 20 | DEP, 20 plus DMP, 20 | 11.7,16.3 |
| CP | ACSP, 30 | Ethyl acetate, 56 | DMP, 14 | 17.6,19.0 |
| CQ | ACSP, 30 | Ethyl acetate, 56 | DEP, 14 | 17.8,19.2 |
| CR | ACSP, 30 | Ethyl acetate, 56 | Butyl lactate, 14 | 18.2 |
| CS | ACSP, 30 | Ethyl acetate, 56 | Triethyl citrate, 14 | 18.4 |
| CT | ACSP, 30 | Ethyl acetate, 56 | 4-Butyrolactone, 14 | 17.2 |
| CU | ACSP, 30 | Ethyl acetate, 56 | Dibutyl phthalate, 14 | 19.6 |
| CV | ACSP, 30 | Ethyl acetate, 56 | Phosflex 500[1], 14 | 19.6 |
| CW | ACSP, 30 | Ethyl acetate, 56 | Tricresyl phosphate, 14 | 19.4 |
| CX | ACSP, 30 | Ethyl acetate, 56 | Texanol[2], 14 | 18.6 |
| CY | ACSP, 40 | Ethyl acetate, 46 | 4-Butyrolactone, 14 | 16.9 |
| CZ | ACSP, 40 | Ethyl acetate, 46 | DMP, 14 | 17.4,19.0 |
| DA | ACSP, 40 | Ethyl acetate, 46 | DEP, 14 | 17.6,19.2 |
| DB | ACSP, 40 | Ethyl acetate, 46 | Triethyl citrate, 14 | 18.3 |
| DC | ACSP, 30 | DMP, 35 | Acetonitrile, 35 | 11.5,18.0 |
| DD | ACSP, 30 | Propylene carbonate, 70 | — | 9,17 |
| DE | ATASP[3], 30 | Propylene carbonate, 70 | — | 9,17 |
| DF | ACSP, 30 | Toluene, 55 | 4-Butyrolactone, 15 | 20.2 |
| DG | ACSP, 30 | DMP, 55 | Propylene carbonate, 15 | 11.4,18.6 |
| DH | ACSP, 30 | DMP, 35 | Propylene carbonate, 35 | 10.5,18.0 |
| DI | ACSP, 40 | DMP, 30 | Propylene carbonate, 30 | 10.5,18.0 |
| DJ | ACSP, 30 | $CH_2Cl_2$, 35 | Propylene carbonate, 35 | 14.5,18.5 |
| DK | ACSP, 30 | Ethyl acetate, 35 | Propylene carbonate, 35 | 14.0,18.0 |
| DL | ACSP, 40 | Propylene carbonate, 60 | — | 9,17 |
| DM | ACSP, 30 | DMP, 23.3 | DEP, 23.3 plus EMP[6] 23.3 | 12,20 |

[1] Phosflex 500 - A chlorinated triaralkyl phosphate, manufactured by Stauffer Chemical Company.
[2] Texanol - The monoisobutyrate of 2,4,4-trimethyl-1,3-pentandiol, manufactured by the Eastman Kodak Company.
[3] ATASP - Acetyl t-amylsulfonyl peroxide.
[4] ATBSP - Acetyl t-butylsulfonyl peroxide.
[5] ACMPSP - Acetyl 3-chloro-1-methylpropylsulfonyl peroxide.
[6] EMP - Ethyl methyl phthalate Table III summarized various unattractive liquid acyl alkylsulfonyl peroxide formulations which are derived from solid acyl alkylsulfonyl peroxides and which satisfy some but not all of the criteria for the novel improved liquid acyl alkylsulfonyl peroxide formulations; therefore, they do not come under the definition of this invention. EA and EB satisfy M number and boiling point criteria but do not satisfy the complete solidification temperature criterion; hence, the phase stabilities of EA and EB are poor compared to the invention compositions at low temperatures. Composition EA is similar to the current liquid ACSP formulation (28–30% ACSP/70–72% DMP). Also failing the comlete solidification temperature criterion are compositions EF, EJ and EK. Compositions EC, ED, EE, EF and EG fail the M number criterion whereas compositions EC, EF, EH, and EI fail the boiling point criterion.

VINYL POLYMERIZATIONS

In the free-radical initiated polymerizations or copolymerizations of ethylenically unsaturated monomers at suitable temperatures (and pressures), the improved liquid acyl alkylsulfonyl peroxide compositions of this invention are found to be effective initiators with respect to efficiency. Ethylenically unsaturated monomers include:

1. olefins, such as ethylene, propylene, stryrene, alphamethylstyrene, chlorostyrene, vinyltoluene, vinyl benzyl chloride, vinyl pyridine and divinylbenzene;
2. diolefins, such as 1,3-butadiene, isoprene and chloroprene;
3. vinyl esters, such as vinyl acetate, vinyl propionate, vinyl laurate, vinyl benzoate and divinyl carbonate;

Table III
Unattractive Acyl Alkylsulfonyl Peroxide Formulations Derived from Solid Acyl Alkylsulfonyl Peroxides

| Composition | Peroxide, % | Solvent, % | C.S.T.[1] ° C | B.P. ° C | M Number |
|---|---|---|---|---|---|
| EA | ACSP, 30 | DMP, 70 | 2 | 283 | 12,19 |
| EB | ACSP, 30 | DEP, 70 | −0.3 | 295 | 13,20 |
| EC | ACSP, 30 | Isobutyl isobutyrate, 70 | −81 | 149 | 23 |
| ED | ACPS, 30 | DBP, 70 | −35 | 325 | 22 |
| EE | ACSP, 30 | DBP, 35 / Isobutyl isobutyrate, 35 | −35 / −81 | 325 / 49 | 22.5 |
| EF | ACSP, 30 | Cyclohexane, 70 | 6.6 | 80.7 | 8 |
| EG | ACSP, 30 | Ethylene glycol, 70 | −13 | 197 | 2 |
| EH | ACSP, 30 | Methylene chloride, 70 | −97 | 40 | 20 |
| EI | ACSP, 30 | Ethyl acetate, 70 | −84 | 77 | 19 |
| EJ | ATASP, 30 | DMP, 70 | 2 | 283 | 12,19 |
| EK | ATASP, 30 | DEP, 70 | −0.3 | 295 | 13,20 |

[1] C.S.T. - Complete Solidifcation Temperature 4. unsaturated nitriles, such as acrylonitrile and methacrylonitrile 5. acrylic acid, methacrylic acid and their esters and amides, such as methyl, ethyl, n-butyl and 2-ethylhexyl acrylates and methacrylates, and acrylamide and methacrylamide; maleic anhydride;

6. maleic and fumaric acids and their esters;

7. vinyl halo and vinylidene halo compounds, such as, vinyl chloride, vinyl bromide, vinyl fluoride, vinylidene chloride and vinylidene fluoride;

8. perhalo olefins, such as tetrafluoroethylene, hexafluoropropylene and chlorotrifluoroethylene;

9. vinyl ethers, such as methyl vinyl ether, ethyl vinyl ether and n-butyl vinyl ether;

10. allyl esters, such as allyl acetate, allyl benzoate, diallyl phthalate, allyl ethyl carbonate, triallyl phosphate, diallyl fumarate, diallyl carbonate, and oxydiethylene bis(allyl carbonate):

11. acrolein;

12. methyl vinyl ketone; and 13. mixtures thereof.

Temperatures of 0° to 80° C, preferably 30° to 65° C, and pure peroxide levels of 0.0005 to 2.0%, preferably 0.01 to 1.0%, can be employed in these polymerization or copolymerization processes. Polymerizations can be carried out in suspension, emulsion, bulk or solution.

These improved liquid acyl alkylsulfonyl peroxide compositions can also be advantageously employed for rapid gellation of unsaturated polyester resins without subsequent curing of the unsaturated polyester resins. In addition, the improved liquid acyl alkylsulfonyl peroxide compositions can be employed as latent generators of acid. Therefore, they can be used to generate acid catalysts.

DESCRIPTION OF PREFERRED EMBODIMENTS

The following are the general procedures that can be employed for the preparation of the compositions of this invention:

Procedure A A neat, i.e., substantially pure, solid acyl alkylsulfonyl peroxide is blended with the liquid solvent system at about 0° C to about 20° C using adequate cooling. A clear liquid formulation is readily obtained. This is one method for producing liquid acyl alkylsulfonyl peroxide formulations from solid acyl alkylsulfonyl peroxides and water soluble solvents or water soluble solvent systems.

Because of the hazard of handling pure sulfonyl peroxides, the following are safer procedures for producing these compositions:

Procedure B

The sulfoxidation of an alkane in the presence of a carboxylic anhydride results in the formation of an oily product mixture containing 50 to 60% of the acyl alkylsulfonyl peroxide. This oily product is then added to water at 10° C or lower in order to precipitate the solid acyl alkylsulfonyl peroxide. This solid is then washed with water in order to remove impurities. The solid is then dissolved in a solvent or solvent mixture, water is separated off and the solution is washed with water at 0° to 10° C. The solution is then dried resulting in a clear solution. The composition can then be adjusted as desired by adding a solvent or solvent mixture. Water insoluble solvents are usually employed in this procedure, although water soluble solvents can be added during or after the drying step.

Procedure B-1

A wetted solid acyl alkylsulfonyl peroxide which has been washed free of impurities is used in this procedure. To the wetted solid is added a solvent or solvent mixture. After solution occurs the water layer is separated and the product is dried. After separated of the desiccant by filtration a clear solution is obtained. This procedure can be used when two water insoluble solvents or when a water soluble and a water insoluble solvent are employed.

Procedure C

The same method as employed in Procedure B-1 is used in this procedure except that when a water soluble solvent is used in conjunction with water insoluble solvent the water insoluble solvent is first added to the wetted solid sulfonyl peroxide, water is separated off, anhydrous $MgSO_4$ is added and stirred, then the water soluble solvent is added prior to filtration.

Procedure D

The same method as employed in Procedure C is used in this procedure except that a water soluble solvent or solvent system is added to the liquid product after separating the desicant by filtration.

Procedure E

The same method as employed in Procedure B is used in this procedure except that a low boiling water insoluble solvent such as methylene chloride or ethyl acetate is used to initially prepare a dried dilute solution of the solid acyl alkylsulfonyl peroxide. Then the desired solvent or solvent system is added and the initially employed low boiling solvent is partially or completely removed in vacuo at 0° to 20° C, thus leaving a clear liquid. This procedure is a safe method for producing improved liquid acyl alkylsulfonyl peroxide formulations from solid acyl alkylsulfonyl peroxides and water soluble solvents and solvent mixtures.

Procedure F

The same as Procedure B except that a solution of 40–60% solid acyl alkylsulfonyl peroxide in a low boiling water insoluble solvent is initially prepared. Then the composition is adjusted by adding another or solvent mixture and additional low boiling solvent, if necessary.

EVALUATION OF COMPOSITIONS

The various compositions were evaluated by these criteria: The physical state of the composition at 0° C and lower. The sensitivity of the composition to impact shock. The so-called Pressure Vessel Test. Loss of assay, i.e., decrease in peroxy oxygen content, on storage in a closed container at constant temperature. The rapid heat test temperature and the burning character of these formulations were also evaluated. Pressure vessel test (PVT): The tester consisted of a cylindrical steel vessel (235 cc. volume) with a variable aperture disc in the side wall, closed at the top with a rupture disc. An aluminum rupture disc, crowned in shape, prestressed to 90% of its burst strength and rated at 98–100 p.s.i.g. was used. There are 74 discs varying in an exponential progression from 1 mm. to 24 mm.

On rapidly heating a material in the tester, the disc bursts or remains intact, depending on the force developed by the decomposition and the amount of venting supplied by the bore in the particular aperture disc used. The bore size of the disc needed to prevent disc rupture is a measure of the violence of the decomposition and the amount of gas generated.

It was determined that a 5.0 g. sample gave reproducible results; these could be used for comparative purposes. Because it is a well-known, widely used, and well-tested material, benzoyl peroxide (98% purity) was tested a provide a base line; the rupture disc burst at 14.9 mm. vent aperture.

Impact shock sensitivity test (ISST).

A modified Du Pont impact testing apparatus was used. In these tests a 5.0 kilogram weight was dropped on the sample a measured distance to determine impact shock sensitivity. Sensitivity to impact shock is shown by noise (report), smoke, or by obvious decomposition of the sample. The maximum drop of the apparatus was 36 inches.

Loss of assay.

In this test, a sample of the peroxide was placed in a closed glass bottle and held in a constant temperature container for 4 weeks. Then the peroxide was analyzed (assayed) for peroxy oxygen content. The arithmetic difference between the original assay of the sample and the final assay of the sample multiplied by 100% and divided by the original assay of the sample is reported as % of assay lost.

The rapid heat test temperature was determined by placing one gram of the composition in a 15 × 150 mm. test tube and heating the contents at a rate of 1° C/min. until the composition vigorously decomposed. The temperature at which this occurred was the rapid heat temperature.

The burning character of the formulation was determined by placing 5 g. of liquid composition in a small aluminum pan (45 mm. wide, 12.5 mm. deep) and touching the liquid formulation with a flame. The time required for ignition, the time of active burning, the time of non-peroxidic burning (other burning) and the maximum flame height were noted.

Several of the compositions of this invention were evaluated in vinyl chloride suspension polymerizations. (described more fully later).

EXAMPLE I

Phase Stabilities, Residue Impact Shock Sensitivities and Safety Test Results of Various 30% ACSP/Methylene Chloride/Cosolvent Formulations These ACSP formulations were prepared by Procedure F in which methylene chloride was used as the low boiling water insoluble solvent. None of the formulations as made were sensitive to impact shock since the formulations contained 70% diluent and 30% peroxide. The residue impact shock sensitivity was determined in the following manner: At 25° C 5.0 g. of the 30% ACSP/methylene chloride/consolvent formulation was placed in a Petri dish (3.5 inches in diameter) and the formulation was exposed to the atmosphere for 4 hours at 25° C. The impact shock sensitivity of the residue was then determined. These results and phase stability results at −20° C and −50° C after 17 weeks are shown in Example I Table A. If the formulation remained a liquid at the test temperature it was given a "pass" grading whereas if solidification occurred it was given a "fail" grading. In the case of the residue impact shock sensitivity test "+" meant that the formulation residue was sensitive to shock whereas "−" meant that the formulation residue was not sensitive to shock.

The residue impact shock sensitivity test results show that a cosolvent possessing a boiling point of at least 165° C is required to produce a liquid acyl alkylsulfonyl peroxide formulation having acceptable residue impact shock (not shock sensitive at 12″). In addition, the formulation should contain about 7% by weight of the solvent boiling above 165° C. When no cosolvent was employed the residue was quite shock sensitive. The improved liquid ACSP formulations listed in Example I Table A were low viscosity liquids at −50° C whereas the commercial ACSP formulation, i.e., 28–30% ASCP/70–72% DMP, was a solid at −50° C. Although the commercial ACSP formulation passed the phase stability test at −20° C it solidified at slightly lower temperature (−23° C). Hence its storage phase stability at −20° C was borderline.

Example I Table B summarizes selected safety test results and thermal stability test results for 30% ACSP/56% methylene chloride/14% cosolvent formulations in which the cosolvent was DMP, dibutyl phthalate (DBP), 4-butyrolactone or Phosflex 500. Also included in Example I Table B are results for the commercial liquid ACSP formulation (28–30% ACSP/70–72% ACSP) and 30% ACSP/70% methylene chloride (the control).

This safety test results show that the improved liquid acyl alkylsulfonyl peroxide formulations, which contain 14% DMP, DBP, 4-butyrolactone and Phosflex 500, have improved safety when compared to the commercial liquid ACSP formulation.

The rapid heat temperatures were higher, maximum flame heights were lower and the ignition times (time required to ignite the formulation) were significantly longer. The thermal stabilities of these formulations and the commercial liquid ACSP formulation at 0° and −10° C were quite similar whereas these improved liquid acyl alkylsulfonyl peroxide formulations were more stable than was 30% ACSP/70% methylene chloride.

EXAMPLE I TABLE A

30% ACSP/CH$_2$Cl$_2$/Cosolvent Formulations
Phase Stabilities - Residue Impact Shock

| Cosolvent, % | B.P., ° C | Phase Stabilities >17 Wks. | | Residue Impact Shock | | | | | |
|---|---|---|---|---|---|---|---|---|---|
| | | −20° C | −50° C | 1″ | 3″ | 6″ | 12″ | 24″ | 36″ |
| Toluene, 7[1.] | 111 | Pass | Pass | − | + | + | + | + | + |
| Toluene, 14[2.] | 111 | Pass | Pass | − | + | + | + | + | + |
| n-Butyl Acetate, 7[1.] | 125 | Pass | Pass | − | + | + | + | + | + |
| n-Butyl Acetate, 14[2.] | 125 | Pass | Fail | − | + | + | + | + | + |
| 4-Butyrolactone, 7[1.] | 204 | Pass | Pass | − | − | − | − | + | + |
| 4-Butyrolactone, 14[2.] | 204 | Pass | Pass | − | − | − | − | − | − |
| Butyl Lactate, 7[1.] | 160–190 | Pass | Pass | − | + | + | + | + | + |
| Butyl Lactate, 14[2.] | 160–190 | Pass* | Pass* | − | − | − | − | − | − |
| Ethyl Lactate, 7[1.] | 154 | Pass | Pass | − | + | + | + | + | + |
| Ethyl Lactate, 14[2.] | 154 | Pass* | Pass* | + | + | + | + | + | + |
| Triethyl Citrate, 7[1.] | 294 | Pass | Pass | + | + | + | + | + | + |
| Triethyl Citrate, 14[2.] | 294 | Pass | Pass* | − | − | − | − | − | − |

EXAMPLE I TABLE A-continued

30% ACSP/CH₂Cl₂/Cosolvent Formulations
Phase Stabilities - Residue Impact Shock

| Cosolvent, % | B.P., °C | Phase Stabilities >17 Wks. | | Residue Impact Shock | | | | | |
|---|---|---|---|---|---|---|---|---|---|
| | | −20° C | −50° C | 1" | 3" | 6" | 12" | 24" | 36" |
| DMP, 14[2.] | 283 | Pass | Pass* | − | − | − | − | − | − |
| DBP, 14[2.] | 192/10 | Pass | Pass* | − | − | − | − | − | − |
| Phosflex 500, 14[2.] | >200 | Pass | Pass | − | − | − | − | − | − |
| Tricresyl Phosphate, 14[2.] | 265/10 | Pass | Pass | − | − | − | − | − | − |
| Texanol, 14[2.] | 180/125 | Pass | Pass | − | − | − | − | − | − |
| Diisobutyl Ketone, 14[2.] | 163-173 | Pass | Fail | + | + | + | + | + | + |
| Isobutyl Isobutyrate, 14[2.] | 144-151 | Pass* | Fail | + | + | + | + | + | + |
| None (Control)[3.] | — | Pass | Pass | − | + | + | + | + | + |
| 28-30% ACSP/70-72% DMP | — | Pass | Fail | − | − | − | − | − | − |

*slight precipitate
[1.]Formulation contained 30% ACSP/63% CH₂Cl₂/7% Cosolvent
[2.]Formulation contained 30% ACSP/56% CH₂Cl₂/14% Cosolvent
[3.]Formulation contained 30% ACSP/70% CH₂Cl₂

EXAMPLE I TABLE B

STABILITY AND SAFETY TESTS - 30% ACSP/CH₂Cl₂/COSOLVENT FORMULATIONS

| COSOLVENT | DMP[1.] | None[2.] | DMP[3.] | DBP[3.] | 4-Butyro-[3.] Lactone | Phosflex[3.] 500 |
|---|---|---|---|---|---|---|
| % Cosolvent | 70-72 | — | 14 | 14 | 14 | 14 |
| Shock Sensitivity | Neg. 20" | Neg. 20" | Neg. 20" | Neg. 20" | Neg. 20" | Neg. 20" |
| Rapid Heat, °C | 55 | 71 | 75 | 75 | 71 | 70 |
| PVT No., mm. | <2.0 | 5.0 | <2.0 | <2.0 | <2.0 | <2.0 |
| Burning Characteristics | | | | | | |
| a) Ignition | 4 secs. | 140 secs. | 70 secs. | 70 secs. | 65 secs. | 60 secs. |
| b) Active Burn. | 1 sec. | Violent puff after ignition, self-extinguishing | 3 secs. | 1 sec. | 3 secs. | 3 secs. |
| c) Other Burn. | 120 secs. | | 5 secs. | 5 secs. | 5 secs. | 5 secs. |
| d) Max. Flame Ht. | 4 ft. | | 2 ft. | 2 ft. | 2 ft. | 2 ft. |
| Thermal Stabilities | | | | | | |
| % of Assay Loss, | | | | | | |
| 0° C/4 wks. | 8.8 | — | 12.2 | 10.7 | 5.4 | 5.3 |
| −10° C/4 wks. | 0.0 | 6.6 | 0.7 | 0.0 | 0.0 | 0.0 |

[1.]Formulation contained 28-30% ACSP/70-72% DMP.
[2.]Formulation contained 30% ACSP/70% CH₂Cl₂.
[3.]Formulation contained 30% ACSP/56% CH₂Cl₂/14% cosolvent.

EXAMPLE II

Phase Stabilities, Residue Impact Shock Sensitivities and Safety Test Results of Various 35 and 40% ACSP/Methylene Chloride/Cosolvent Formulations.

These ACSP formulations were prepared to the procedure described in Example 1. None of the formulations as made were sensitive to impact shock and all were low viscosity liquids at −20° C. Phase stabilities after 13 weeks at −20° and −50° C and residue impact shock sensitivities are summarized in Example II Table A. In general, only the formulations with no high boiling solvent were sensitive to residue impact shock. All of the improved liquid ACSP formulations passed the −20° C phase stability test whereas all failed the −50° C phase stability test. Hency they appear to have phase stabilities similar to the commercial liquid ACSP formulation. However, since higher ACSP levels (35 and 40%) are possible with the solvent systems employed the improved liquid 35 and 40% ACSP formulations are superior to the commercial liquid ACSP formulation. They also have lower viscosities than the commercial liquid ACSP formulation.

Example II Table B summarizes stability results and selected safety results for several improved liquid 35% ACSP/51% CH₂Cl₂/14% cosolvent formulations. Example II Table C summarizes similar results for several improved liquid 40% ACSP/46% CH₂Cl₂/14% cosolvent formulations. These formulations have about the same stability as the commercial liquid ACSP formulation and have better safety results (rapid heat temperatures and maximum flame heights) than the commercial liquid ACSP formulation.

EXAMPLE II TABLE A

35% and 40% ACSP/CH₂Cl₂/Cosolvent Formulatons
Phase Stabilities - Residue Impact Shock

| Cosolvent | ACSP % | Phase Stabilities (13 wks.) | | Residue Impact Shock | | | |
|---|---|---|---|---|---|---|---|
| | | −20° C | −50° C | 3" | 6" | 12" | 36" |
| 4-Butyrolactone, 14 | 35[1.] | Pass | Fail | − | − | − | − |
| 4-Butyrolactone, 14 | 40[2.] | Pass | Fail | − | − | − | − |
| DBP, 14 | 35[1.] | Pass | Fail | − | − | − | − |
| DBP, 14 | 40[2.] | Pass | Fail | − | − | − | − |
| Triethyl Citrate, 14 | 35[1.] | Pass | Fail | − | − | − | − |
| Triethyl Citrate, 14 | 40[2.] | Pass | Fail | − | − | − | − |
| DMP, 14 | 35[1.] | Pass | Fail | − | − | − | − |
| DMP, 14 | 40[2.] | Pass | Fail | − | − | − | − |
| Butyl Lactate, 14 | 35[1.] | Pass | Fail | − | − | − | − |
| Butyl Lactate, 14 | 40[2.] | Pass | Fail | − | − | − | − |
| Dibutyl Maleate, 14 | 35[1.] | Pass | Fail | − | − | − | − |
| Dibutyl Maleate, 14 | 40[2.] | Pass | Fail | − | − | − | + |
| Dioctyl Adipate, 14 | 35[1.] | Pass | Fail | − | − | − | − |
| Dioctyl Adipate, 14 | 40[2.] | Pass | Fail | − | + | + | + |

EXAMPLE II TABLE A-continued

35% and 40% ACSP/CH$_2$Cl$_2$/Cosolvent Formulatons
Phase Stabilities - Residue Impact Shock

| Cosolvent | ACSP % | Phase Stabilities (13 wks.) −20° C | −50° C | Residue Impact Shock 3" | 6" | 12" | 36" |
|---|---|---|---|---|---|---|---|
| Phosflex 500, 14 | 35[1.] | Pass | Fail | — | — | — | — |
| Phosflex 500, 14 | 40[2.] | Pass | Fail | — | — | — | — |
| None (CH$_2$Cl$_2$ only) | 35[1.] | Pass | Borderline | + | + | + | + |
| None (CH$_2$Cl$_2$ only) | 40[2.] | Borderline | Fail | + | + | + | + |
| 28-30% ACSP/70-72% DMP | | Pass | Fail | — | — | — | — |

[1.] Formulation contained 35% ACSP/51% CH$_2$Cl$_2$/14% cosolvent.
[2.] Formulation contained 40% ACSP/46% CH$_2$Cl$_2$/14% cosolvent

EXAMPLE II TABLE B

STABILITY AND SAFETY TESTS - 35% ACSP/CH$_2$Cl$_2$
COSOLVENT FORMULATIONS

| COSOLVENT | DMP[1.] | 4-Butyrolactone[2.] | DBP[2.] | Phosflex 500[2.] |
|---|---|---|---|---|
| % Cosolvent | 70-72 | 14 | 14 | 14 |
| Shock Sensitivity | Neg. 20" | Neg. 20" | Neg. 20" | Neg. 20" |
| Rapid Heat Temp., ° C | 55 | 73 | 72 | 70 |
| PVT No., mm. | <2.0 | <2.0 | <2.0 | <2.0 |
| Burning Character | | | | |
| a) Ignition | 4 secs. | 8 secs. | 15 secs. | 15 secs. |
| b) Active Burn. | 1 sec. | 1 sec. | 1 sec. | 1 sec. |
| c) Other Burn. | 120 sec. | 24 secs. | 24 secs. | 23 secs. |
| d) Max. Flame Ht. | 4 ft. | 3 ft. | 3 ft. | 3 ft. |
| Thermal Stabilities | | | | |
| % of Assay loss, | | | | |
| 0° C/4 wks. | 8.8 | 7.5 | 14.0 | 9.4 |
| −10° C/4 wks. | 0.0 | 0.9 | 2.0 | 1.1 |

[1.] Formulation contained 28-30% ACSP/70-72% DMP.
[2.] Formulation contained 35% ACSP/51% CH$_2$Cl$_2$/14% cosolvent.

EXAMPLE II TABLE C

STABILITY AND SAFETY TESTS - 40% ACSP/CH$_2$Cl$_2$/
COSOLVENT FORMULATIONS

| COSOLVENT | DMP[1.] | 4-Butryolactone[2.] | DBP[2.] | Phosflex 500[2.] |
|---|---|---|---|---|
| % Cosolvent | 70-72 | 14 | 14 | 14 |
| Shock Sensitivity | Neg. 20" | Neg. 20" | Neg. 20" | Neg. 20" |
| Rapid Heat Temp., ° C | 55 | 69 | 68 | 70 |
| PVT No., mm. | <2.0 | >2<3 | <2.0 | >2<3 |
| Burning Character | | | | |
| a) Ignition | 4 secs. | 5 secs. | 4 secs. | 3 secs. |
| b) Active Burn. | 1 sec. | 1 sec. | 1 sec. | 1 sec. |
| c) Other Burn. | 120 secs. | 14 secs. | 20 secs. | 20 secs. |
| d) Max. Flame Ht. | 4 ft. | 3 ft. | 3 ft. | 3 ft. |
| Thermal Stabilities | | | | |
| % of Assay Loss, | | | | |
| 0° C/4 wks. | 8.8 | 6.3 | 13.2 | 9.1 |
| −10° C/4 wks. | 0.0 | 0.0 | 0.0 | 0.0 |

[1.] Formulation contained 28-30% ACSP/70-72% DMP.
[2.] Formulation contained 40% ACSP/46% CH$_2$Cl$_2$/14% cosolvent.

EXAMPLE III

Phase Stabilities of Various 30% ACSP/55% DMP/15% Cosolvent Formulations

These improved liquid ACSP formulations were prepared by the method described in Procedure E. Example III Table A summarizes −20° C and −32° C phase stabilities of these improved liquid ACSP formulations after 10 weeks. The results show that these improved liquid ACSP formulations have superior phase stabilities at −32° C than the commercial liquid ACSP formulation. The improved liquid ACSP formulations which were stored at −32° C for 10 weeks were then placed in a −45° C storage chest for an additional 6 weeks. The phase stability results are summarized in Example III Table B. These results show that the 30% ACSP/55% DMP/15% cosolvent formulation in which the cosolvent was dimethylacetamide, 4-butyrolactone or diethyl phthalate remained phase stable after an additional 6 weeks at −45° C.

EXAMPLE III TABLE A

Phase Stabilities of Various 30% ACSP/55% DMP/15% Cosolvent Formulations

| Cosolvent (15%) | Phase Stabilities after 10 Weeks at −20° C | −32° C |
|---|---|---|
| Diacetone alcohol | Pass | Pass |
| Tetrahydrofurfuryl alcohol | Pass | Pass |
| Ethyl acetoacetate | Pass | Pass |
| Tetramethylurea | Pass | Pass |
| Hexamethylphosphoramide | Pass | Pass |
| Dimethylacetamide | Pass | Pass |
| N-Methyl-2-pyrrolidone | Pass | Pass |
| 4-Butyrolactone | Pass | Pass |
| Triethyl citrate | Pass | Pass |
| Butyl lactate | Pass | Pass |
| Dioctyl adipate | Pass | Pass |
| Diethyl phthalate | Pass | Pass |
| DMP[1.] | Pass | Fail (solid) |

[1.] 28-30% ACSP/70-72% DMP (the commercial liquid ACSP formulation)

EXAMPLE III TABLE B

Phase Stabilities of Various 30% ACSP/55% DMP/
15% Cosolvent Formulations

| Cosolvent (15%) | Phase Stabilities after 16 Weeks at | |
|---|---|---|
| | −20° C | −32° C to −45° C |
| Diacetone alcohol | Pass | Fail |
| Tetrahydrofurfuryl alcohol | Pass | Fail |
| Ethyl acetoacetate | Pass | Fail |
| Tetramethylurea | Pass | Fail |
| Hexamethylphosphoramide | Pass | Fail |
| Dimethylacetamide | Pass | Pass[2] |
| N-Methyl-2-pyrrolidone | Pass | Fail |
| 4-Butyrolactone | Pass | Pass |
| Triethyl citrate | Pass | Fail |
| Butyl lactate | Pass | Fail |
| Dioctyl adipate | Pass | Fail |
| Diethyl phthalate | Pass | Pass |
| DMP[1] | Pass | Fail |

[1] 28-30% ACSP/70-72% DMP (the commercial liquid ACSP formulation).
[2] Very slight solids observed.

EXAMPLE IV

Phase Stabilities of 30% ACSP/35% DMP/35% DEP, 30% ACSP/ 70% 4-Butyrolactone and 30% ACSP/52.5% DMP/17.5% 4-Butyrolactone Formulations These improved liquid ACSP formulations were prepared by the method described in Procedure E. Also prepared by this method were 30% ACSP/70% DBP and 30% ACSP/70% DEP. Phase stabilities were determined on these ACSP formulations at −50° C after 9 weeks. The results are summarized in Example IV Table. These results show that

EXAMPLE IV TABLE

−50° C Phase Stabilities of Various Liquid 30% ACSP Formulations

| Solvent, % | Cosolvent, % | Phase Stabilities after 9 weeks at −50° C |
|---|---|---|
| DMP, 70[1] | None | Fail (solid) |
| DBP, 70 | None | Fail (solid)[2] |
| DEP, 70 | None | Fail (solid) |
| 4-Butyrolactone, 70 | None | Pass (slightly viscous liquid) |
| DMP, 35 | DEP, 35 | Pass (glass-like liquid) |
| DMP, 52.5 | 4-Butyrolactone, 17.5 | Pass (liquid) |

[1] Similar to the commercial liquid ACSP formulation.
[2] Failed after 4 weeks at −18° C 4-butyrolactone is a very good solvent for ACSP when used alone or in combination with DMP. In addition use of DMP or DEP alone results in solid formation at −50° C (with DBP solidification occurred at −18° C) whereas use of a 1/1 mixture of DMP and DEP produced a phase stable 30% ACSP solution at −50° C. The latter result was not expected since one would not normally expect the solubility of ACSP in a mixture of solvents to be better than the solubility of ACSP in either solvent alone (in this case the −50° C phase stability is a qualitative measure of the ACSP solubility in the solvents or solvent systems employed).

EXAMPLE V

Phase Stabilities of Various 30%, 35%, 40% and 45% ACSP/DMP/DEP Liquid Formulations These improved liquid ACSP formulations were prepared by the method outlined in Procedure B starting with wetted solid ACSP. The solvent mixtures obtained in the final ACSP formulations were those employed during work-up. Phase stabilities at −20° and −45° C after 20 weeks are summarized in Example V Table.

The results showed that mixed solvent systems composed of DMP and DEP produced ACSP liquid formulations that were phase stable at −45° C and had ACSP concentrations of greater than 40% whereas the commercial liquid ACSP formulation (28-30% ACSP/70-72% DMP) and 30% ACSP/70% DEP solidified at −45° C. The results also show that a wide range of DMP/DEP solvent compositions give phase stable liquid ACSP formulations at −45° C.

EXAMPLE V TABLE

30%, 35%, 40% and 45% ACSP/DMP/DEP Formulations

| ACSP, % | DMP, % | DEP, % | Phase Stabilities after 20 wks. | |
|---|---|---|---|---|
| | | | −20° C | −45° C |
| 30[1] | 70 | 0 | Pass | Fail |
| 30 | 62 | 8 | Pass | Fail |
| 30 | 55 | 15 | Pass | Pass |
| 30 | 45 | 25 | Pass | Pass[2] |
| 30 | 35 | 35 | Pass | Pass |
| 30 | 25 | 45 | Pass | Pass |
| 30 | 15 | 55 | Pass | Fail |
| 30 | 0 | 70 | Fail | Fail |
| 35 | 51 | 14 | Pass | Pass |
| 40 | 47 | 13 | Pass | Pass |
| 45 | 43 | 12 | Pass | Pass[2] |

[1] Similar to the commercial liquid ACSP formulation.
[2] Slight solids - borderline phase stability.

EXAMPLE VI

Phase Stabilities of Various Liquid ACSP Formulations at −23° C (−10° F)

Half-gallon samples of 30% ACSP/55% DMP/15% 4-butyrolactone and 30% ACSP/55% DMP/15% DEP were prepared by the method described in Procedure B. These improved liquid ACSP formulations and a gallon sample of the commercial liquid ACSP formulation (28-30% ACSP/70-72% DMP) were phase stability tested at −23° C (−10° F) for 16 weeks. Both improved liquid ACSP formulations remained liquid at −23° C (−10° F) over the test period whereas the commercial liquid ACSP formulation solidified after two weeks at −23° C (−10° F).

EXAMPLE VII

Phase Stabilities of Miscellaneous Improved Liquid ACSP Formulations at −10° C and −25° C 20%, 30%, 40% and 44% ACSP formulations in a 1/1 solvent mixture of DMP and acetone were prepared from wetted solid ACSP (60-65%) using Procedure B-1. Other formulations which were prepared by this procedure were 30% ACSP/35% DMP/35% ethyl acetate and 35% ACSP/32.5% DMP/32.5% $CH_2Cl_2$. Phase stability results at −10° and −25° C after 4 weeks are summarized in Example VII Table. The results showed that all of the above improved liquid ACSP formulations had better phase stabilities at −25° C than the commercial liquid ACSP formulation.

EXAMPLE VII TABLE

Phase Stabilities of Miscellaneous Improved ACSP Formulations

| ACSP, % | DMP, % | Cosolvent, % | Phase Stabilities after 4 wks. at | |
|---|---|---|---|---|
| | | | −10° C | −25° C |
| 20 | 40 | acetone, 40 | Not done | Pass |
| 30 | 35 | acetone, 35 | Pass | Pass |
| 40 | 30 | acetone, 30 | Not done | Pass |
| 44 | 28 | acetone, 28 | Pass | Pass |
| 30 | 35 | ethyl acetate, 35 | Pass | Pass |
| 35 | 32.5 | $CH_2Cl_2$, 32.5 | Pass | Pass |

EXAMPLE VII TABLE-continued
Phase Stabilities of Miscellaneous Improved ACSP Formulations

| ACSP, % | DMP, % | Cosolvent, % | Phase Stabilities after 4 wks. at | |
|---|---|---|---|---|
| | | | −10° C | −25° C |
| 28–30[1] | 70–72 | None | Pass | Fail[2] |

[1] Corresponds to the commercial liquid ACSP formulation.
[2] Solid after two weeks at −23° C (see Example VI).

EXAMPLE VIII

Processes for Preparing 30% ACSP/55% DMP/15% 4-Butyrolactone

The objective of this example was to determine the best method for preparation of 30% ACSP/55% DMP/15% 4-butyrolactone. The first sample (1) was prepared by dissolving washed, wetted solid ACSP with a 55/15 mixture of DMP and 4-butyrolactone followed by MgSO$_4$ drying. The second sample (2) was prepared by Procedure C whereas the third sample (3) was prepared by Procedure D. The three samples of 30% ACSP/55% DMP/15% 4-butyrolactone were then stored at −45° C for 4 days. The appearance of the samples at −45° C was then recorded. The results are summarized below and show that Procedure 30% ACSP/55% DMP/15% 4-Butyrolactone Samples

| Sample | Preparative Procedure | Appearance after 4 days at −45° C |
|---|---|---|
| (1) | B-1 | Cloudy-water crystals |
| (2) | C | Clear liquid |
| (3) | D | Clear liquid |

C and D were the best preparative methods when 4-butyrolactone was empllyed as a cosolvent in these improved ACSP formulation. Apparently 4-butyrolactone has a great affinity for water.

EXAMPLE IX

Phase Stabilities of Improved Liquid 30% Acetyl t-Amyl-Sulfonyl Peroxide (ATASP)/DMP/Cosolvent Formulations 30% ATASP/70% DMP (a prior art composition) and 30% ATASP/35% DMP/35% DEP were prepared by Procedure B whereas 30% ATASP/55% DMP/15% 4-butyrolactone was prepared by Procedure D. Phase stability results at −20° C and −32° C after 15 weeks are summarized in Example IX Table and show that the improved liquid 30% ATASP formulations have phase stabilities at −32° C which are superior to those of the prior art composition (30% ATASP/70% DMP).

EXAMPLE IX TABLE
Phase Stabilities of Improved Liquid 30% ATASP Formulations

| ATASP, % | DMP, % | Cosolvent, % | Phase Stabilities after 15 wks. at | |
|---|---|---|---|---|
| | | | −20° C | −32° C |
| 30[1] | 70 | None | Pass | Fail (solid) |
| 30 | 35 | DEP, 35 | Pass | Pass |
| 30 | 55 | 4-Butyrolactone, 15 | Pass | Pass |

[1] Prior art composition.

EXAMPLE X

50° C/8 Hours Vinyl Chloride Suspension Polymerization Efficiencies of Improved Liquid ACSP Formulations Several of the improved liquid ACSP formulations described in the Examples above and the commercial liquid ACSP composition (28–30% ACSP/70–72% DMP) were evaluated in vinyl chloride suspension polymerizations at 50° C/8 hours. The following recipe was employed in these polymerizations:

| Ingredient | Parts by Weight |
|---|---|
| Vinyl chloride monomer | 100 |
| Water (triple distilled) | 175 |
| Methocel* (65 HG, 50 cps) (1% aqueous soln.) | 60 |
| Aerosol MA** (1% aqueous soln.) | 15 |
| Free-radical initiator | Variable |

*Methylcellulose (Dow Chemical Co.)
**Sodium salt of dihexyl sulfosuccinate (American Cyanamid Co.)

Procedure

Pop bottles were employed. Water, aqueous Methocel and aqueous Aerosol MA were added to each bottle and the contents were frozen at −20° C. The pH of this system was 6.0 to 6.5 at room temperature. It is conceivable that the pH could be varied by the use of buffers so as to maximize or optimize the efficiency of the polymerization. Other suspending agents and/or surfactants (anionic, cationic, nonionic and amphoteric) can be used in place of this suspension system in order to insure that a suspension is maintained throughout the polymerization. To the bottles were then added varying amounts of free-radical initiators (several bottles for each initiator) and the required amount of liquid vinyl chloride monomer (at −14° C). The bottles were crown-capped, enclosed in safety cages and placed in a constant temperature bottle polymerizer maintained at 50° C. End-over-end tumbling at a rate of 25 revolutions per minute was employed for agitation and the polymerizations were allowed to proceed for 8 hours. At the end of that time the bottles were removed from the bottle polymerizer, cooled to 0° C and vented of vinyl chloride monomer. Venting of unreacted vinyl chloride monomer seldom took more than 15 to 30 minutes; hence, postpolymerization was insignificant. The amount of polymer produced was determined gravimetrically (by difference in weight) and plots of initiator required versus % conversion were constructed for each initiator and the amounts of initiators (in grams and in moles) required at 90% conversion were determined from the plots. These results are shown in Example X Table. The results show that the improved liquid ACSP formulations had vinyl chloride polymerization efficiencies similar to those of the commercial liquid ACSP formulation. Apparently the solvents employed had little or no effect on polymerization efficiency. The improved liquid ACSP formulations of this invention were more advantageously employed in vinyl chloride polymerizations than was the commercial liquid ACSP composition owing to their improved handling and storage characteristics (phase stabilities). PVC producers consider the handling and storage characteristics to be important properties of the initiators that they employ.

EXAMPLE X TABLE

50° C/8 Hours Vinyl Chloride Suspension Polymerization Efficiencies

| ACSP, % | Solvent, % | (Cosolvent) Second Solvent, % | Pure ACSP Required/100g VCl at 90% Conversion | |
|---|---|---|---|---|
| | | | Grams | Moles × 10⁴ |
| 28–30[1] | DMP, 70–72 | None | 0.0274–0.0322 | 1.23–1.45 |
| 30 | CH$_2$Cl$_2$, 56 | DMP, 14 | 0.029 | 1.31 |
| 30 | CH$_2$Cl$_2$, 35 | DMP, 35 | 0.025 | 1.12 |
| 30 | CH$_2$Cl$_2$, 56 | DBP, 14 | 0.0258 | 1.16 |
| 30 | CH$_2$Cl$_2$, 56 | 4-Butyrolactone, 14 | 0.0250 | 1.13 |
| 30 | CH$_2$Cl$_2$, 56 | Phosflex 500[2], 14 | 0.0255 | 1.15 |
| 30 | DMP, 55 | DEP, 15 | 0.033 | 1.49 |
| 30 | DMP, 35 | Acetone, 35 | 0.0233 | 1.05 |
| 30 | DMP, 35 | Ethyl Acetate, 35 | 0.0266 | 1.20 |

[1] The commercial liquid ACSP composition.
[2] A chlorinated triaralkyl phosphate manufactured by the Stauffer Chemical Company.

EXAMPLE XI

Phase Stabilities of 30% and 40% ACSP Liquid Formulations using Propylene Carbonate as a Solvent Samples of 30% ACSP/70% propylene carbonate, 40% ACSP/60% propylene carbonate, 30% ACSP/35% propylene carbonate/35% DMP, 30% ACSP/35% propylene carbonate/35% ethyl acetate and 30% ACSP/70% ethyl acetate were prepared by procedure E. The phase stabilities of these formulations at −20° C and −45° C were determined and the results are summarized in Example XI Table. The results show that propylene carbonate alone or in combination with DMP or ethyl acetate is an excellent solvent for ACSP.

Example XI Table

Liquid 30% and 40% ACSP Formulations

| ACSP, % | Solvent, % | Cosolvent, % | Phase Stabilities | | | |
|---|---|---|---|---|---|---|
| | | | Days at −20° C | | Days at −45° C | |
| 30 | Propylene carbonate, 70 | — | 8 | Pass | 8 | Pass |
| 40 | Propylene carbonate, 60 | — | 8 | Pass | 8 | Pass |
| 30 | Propylene carbonate, 35 | Ethyl acetate, 35 | 8 | Pass | 8 | Pass |
| 30 | Propylene carbonate, 35 | DMP, 35 | 8 | Pass | 8 | Pass |
| 30 | Ethyl acetate, 70 | — | 8 | Pass | 4 | Fail* |

*Solid formation

EXAMPLE XII

Phase Stabilities of 30% Liquid ACSP Formulations Prepared with Trisolvent Systems Samples of 30% ACSP/23.3% DMP/23.3% DEP/23.3% ethyl methyl phthalate (EMP) and 30% ACSP/20% 4-butyrolactone/25% DMP/25% DEP were prepared by procedure E. The 1/1/1 DMP/DEP/EMP solvent system used to produce the former formulation was prepared in the following manner:

A mixture of 1.0 mole of phthalic anhydride, 3.0 moles of ethanol, 3.0 moles of methanol and 3.0 g. of 98% H$_2$SO$_4$ was refluxed at 74° C for 10 hours. After working-up by procedures well known in the art a liquid product was obtained which had a composition weight ratio of 22/3/22 for DMP/DEP/EMP according to gas chromatographic analysis. To 50 g of this product was added 20.2 g of DEP. This produced the desired 1/1/1 mixture of DMP/DEP/EMP.

The two 30% liquid ACSP formulations were then phase stability tested at −20° and −45° C for 4 days and were found to be phase stable (remained liquid) at both temperatures.

EXAMPLE XIII

Complete Solidification Temperatures of Solvents and Solvent Mixtures

The complete solidification temperatures (C.S.T.) of various solvents and solvent mixtures were determined. In the case of pure solvents the C.S.T. corresponded to the melting point temperature of the pure solvent as determined in the usual manner. In the case of solvent mixtures the C.S.T. corresponded to the temperature below which a liquid phase was absent and above which a liquid phase was present. The C.S.T. of a solvent mixture was determined by adding about 40 g of solvent mixture to a two ounce clear glass bottle, cooling the sample in a −30° to −35° C bath and scratching the inside of the bottle with a glass thermometer until complete solidification occurred or until the solvent mixture remained liquid or retained a liquid phase after about 1 hour at approximately the bath temperature. In the latter case the C.S.T. was considered to be below the temperature ultimately attained by the solvent mixture. In the former case the C.S.T. was taken as the temperature at which complete solidification occurred.

Example XIII Table summarizes the complete solidification temperatures (C.S.T.) for various solvents and solvent systems which were employed for the preparation of various acyl alkylsulfonyl peroxide formulations derived from solid acyl alkylsulfonyl peroxides. Example XIII Table also states whether or not the solvent or solvent system was used in the improved liquid acyl alkylsulfonyl peroxide formulations of this invention. The results of this example and those of previous examples show that solvent or solvent systems which have complete solidification temperatures (C.S.T.) above about −10° C fail to produce attractive liquid formulations whereas those solvents or solvent mixtures with C.S.T. temperatures below about −10° C produce attractive improved liquid acyl alkylsulfonyl peroxide formulations which are derived from solid acyl alkylsulfonyl peroxides.

Example XIII Table

Complete Solidification Temperatures of Solvents and Solvent Mixtures

| Solvent Parts | Cosolvent, Parts | C.S.T., °C | Solvent or Solvent System for Invention Compositions |
|---|---|---|---|
| DMP, 70 | — | ca. 2 | No |
| DEP, 70 | — | ca. 0 | No |
| DMP, 62 | DEP, 8 | −7 | No |
| DMP, 55 | DEP, 15 | <−28 | Yes |
| DMP, 45 | DEP, 25 | <−28 | Yes |
| DMP, 35 | DEP, 35 | <−28 | Yes |
| DMP, 55 | 4-Butryolactone, 15 | <−28 | Yes |
| DMP, 35 | Ethyl acetate, 35 | <−28 | Yes |
| $CH_2Cl_2$, 56 | DMP, 14 | <−28 | Yes |
| $CH_2Cl_2$, 56 | 4-Butyrolactone, 14 | <−28 | Yes |
| DMP, 35 | Propylene carbonate, 35 | <−28 | Yes |

What is claimed is:

1. A liquid solution composition which is a storable stable liquid at 0° to −40° C consisting essentially of
  a. 10 to 70% by weight of a solid acyl alkylsulfonyl peroxide with a melting point between −10° and 70° C having the formula

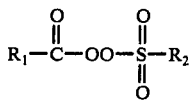

where
  1. $R_1$ is an alkyl of 1 to 4 carbons and
  2. $R_2$ is selected from the group consisting of an alkyl or monochloroalkyl radical of 3 to 18 carbons and a cycloalkyl or cyclomonochloroalkyl radical of 4 to 12 carbons, and
  b. 90 to 30% by weight of a solvent or solvent system having a complete solidification temperature below about −10° C and a miscibility number of greater than 8 and less than 21, which solvent or solvent system possesses at least about 20% by weight based on the solid acyl sulfonyl peroxide of a solvent which has a boiling point of at least 165° C at 760 torr.

2. The composition of claim 1 wherein the solid acyl alkylsulfonyl peroxide is acetyl cyclohexylsulfonyl peroxide.

3. The composition of claim 1 wherein the solid acyl alkylsulfonyl peroxide is acetyl t-amylsulfonyl peroxide.

4. The liquid solution composition of claim 2 wherein the composition consists essentially of in percent by weight of composition
  a. 30% of acetyl cyclohexylsulfonyl peroxide,
  b. 55% of dimethyl phthalate, and
  c. 15% of diethyl phthalate.

5. The liquid solution composition of claim 2 wherein the composition consists essentially of in percent by weight of composition
  a. 35% of acetyl cyclohexylsulfonyl peroxide,
  b. 51% of dimethyl phthalate, and
  c. 14% of diethyl phthalate.

6. The liquid solution composition of claim 2 wherein the composition consists essentially of in percent by weight of composition
  a. 40% of acetyl cyclohexylsulfonyl peroxide,
  b. 47% of dimethyl phthalate, and
  c. 13% of diethyl phthalate.

7. The liquid solution composition of claim 2 wherein the composition consists essentially of in percent by weight of composition
  a. 30% of acetyl cyclohexylsulfonyl peroxide,
  b. 55% of dimethyl phthalate, and
  c. 15% of 4-butyrolactone.

8. The liquid solution composition of claim 2 wherein the composition consists essentially of in percent by weight of composition
  a. 30% of acetyl cyclohexylsulfonyl peroxide,
  b. 56% methylene chloride, and
  c. 14% dimethyl phthalate.

9. The liquid solution composition of claim 2 wherein the composition consists essentially of in percent by weight of composition
  a. 30% of acetyl cyclohexylsulfonyl peroxide,
  b. 56% of methylene chloride, and
  c. 14% of 4-butyrolactone.

10. The liquid solution composition of claim 2 wherein the composition consists essentially of in percent by weight of composition
  a. 30% of acetyl cyclohexylsulfonyl peroxide,
  b. 35% of dimethyl phthalate, and
  d. 35% of ethyl acetate.

11. The liquid solution composition of claim 3 wherein the composition consists essentially of in percent by weight of composition
  a. 30% of acetyl t-amylsulfonyl peroxide,
  b. 35% of dimethyl phthalate, and
  c. 35% of diethyl phthalate.

12. The liquid solution composition of claim 2 wherein the composition consists essentially of in percent by weight of composition
  a. 30% of acetyl cyclohexylsulfonyl peroxide, and
  b. 70% of 4-butyrolactone.

13. The liquid solution composition of claim 2 wherein the composition consists essentially of in percent by weight of composition
  a. 30% of acetyl cyclohexylsulfonyl peroxide, and
  b. 70% of propylene carbonate.

14. The liquid solution composition of claim 2 wherein the composition consists essentially of in percent by weight of composition
  a. 40% of acetyl cyclohexylsulfonyl peroxide, and
  b. 60% of propylene carbonate.

15. The liquid solution composition of claim 2 wherein the composition consists essentially of in percent by weight of composition
  a. 30% of acetyl cyclohexylsulfonyl peroxide,
  b. 35% of propylene carbonate, and
  c. 35% of ethyl acetate.

16. The liquid solution composition of claim 2 wherein the composition consists essentially of in percent by weight of composition
  a. 30% of acetyl cyclohexylsulfonyl peroxide,
  b. 35% of propylene carbonate, and
  c. 35% of dimethyl phthalate.

17. The liquid solution composition of claim 2 wherein the composition consists essentially of in percent by weight of composition
  a. 30% of acetyl cyclohexylsulfonyl peroxide,
  b. 20% of 4-butyrolactone,
  c. 25% of dimethyl phthalate, and
  d. 25% of diethyl phthalate.

18. The liquid solution composition of claim 2 wherein the composition consists essentially of in percent by weight of composition
  a. 30% of acetyl cyclohexylsulfonyl peroxide,
  b. 23.3% of dimethyl phthalate,
  c. 23.3% of diethyl phthalate, and
  d. 23.3% of ethylmethyl phthalate.

* * * * *